United States Patent
Yamaoka et al.

(10) Patent No.: US 7,368,224 B2
(45) Date of Patent: May 6, 2008

(54) PHOTOPOLYMERIZABLE COMPOSITION

(75) Inventors: Tsuguo Yamaoka, Funabashi (JP); Ikuo Shimizu, Yokkaichi (JP); Hiroshi Toyoda, Yokkaichi (JP); Motoharu Kinugasa, Yokkaichi (JP); Masanori Ikuta, Yokkaichi (JP); Kyoko Katagi, Ami-machi (JP)

(73) Assignee: Kyowa Hakko Chemical Co., Ltd., Tokyo (JP)

( * ) Notice: Subject to any disclaimer, the term of this patent is extended or adjusted under 35 U.S.C. 154(b) by 152 days.

(21) Appl. No.: 10/508,528

(22) PCT Filed: Apr. 3, 2003

(86) PCT No.: PCT/JP03/04254

§ 371 (c)(1),
(2), (4) Date: Dec. 6, 2004

(87) PCT Pub. No.: WO03/085005

PCT Pub. Date: Oct. 16, 2003

(65) Prior Publication Data

US 2005/0164120 A1    Jul. 28, 2005

(30) Foreign Application Priority Data

Apr. 8, 2002  (JP) ............... 2002-104616

(51) Int. Cl.
*G03C 1/735* (2006.01)
*G03F 7/028* (2006.01)
*C07D 261/06* (2006.01)
*C07D 231/10* (2006.01)

(52) U.S. Cl. .............. 430/281.1; 430/916; 430/926; 430/285.1; 430/919; 430/920; 430/921; 430/923; 430/925; 548/247; 548/373.1

(58) Field of Classification Search ........... 548/247, 548/373.1
See application file for complete search history.

(56) References Cited

U.S. PATENT DOCUMENTS

| | | | |
|---|---|---|---|
| 4,743,530 A | 5/1988 | Farid et al. ............ 430/281 |
| 4,997,745 A | 3/1991 | Kawamura et al. ..... 430/281 |
| 5,275,917 A | 1/1994 | Inaishi ................... 430/288 |
| 5,681,685 A * | 10/1997 | Yamaoka et al. ..... 430/281.1 |
| 6,596,364 B2 * | 7/2003 | Shimizu et al. ........ 428/64.1 |
| 6,660,867 B2 | 12/2003 | Shimizu et al. ........ 548/105 |
| 6,737,143 B2 * | 5/2004 | Noguchi et al. ....... 428/64.1 |
| 2003/0206514 A1 * | 11/2003 | Noguchi et al. ....... 369/288 |
| 2004/0202098 A1 | 10/2004 | Yashiro et al. ........ 369/288 |

FOREIGN PATENT DOCUMENTS

| | | | |
|---|---|---|---|
| EP | 1113335 A1 * | 7/2001 |
| EP | 0 729 945 | 2/2002 |
| EP | 1 267 338 | 12/2002 |
| EP | 1449890 | 8/2004 |
| JP | 2000-159776 | * 6/2000 |
| JP | 2000-345059 | * 12/2000 |
| JP | 2002-370451 | 12/2002 |
| WO | WO 96/09289 | 3/1996 |
| WO | WO 02/050190 | 12/2001 |

OTHER PUBLICATIONS

Machine-assisted English translation of JP 2000-159776 provided by JPO.*
Machine-assisted English translation of JP 2000-345059 (provided by JPO).*
Tarazi, et al., "Investigation of the spectral properties of a squarylium near-infrared dye and its complexation with Fe(III) and Co(II) ions", *Microchemical Journal*, vol. 64, No. 3 (2000), pp. 247-256.

* cited by examiner

*Primary Examiner*—Sin Lee
(74) *Attorney, Agent, or Firm*—Fitzpatrick, Cella, Harper & Scinto

(57) ABSTRACT

The invention provides a photopolymerizable composition having a high photosensitivity, which comprises a metal complex of a squarylium compound, a radical generator, and a compound having at least one ethylenically unsaturated double bond.

The photopolymerizable composition of the present invention is advantageously used for a visible laser recording material such as a PS (Presensitized Plate) for laser direct plate-making, a dry film resist, a digital proof, a hologram, or the like, a panchromatic sensitive material (e.g., a sensitive material for a color hologram and a sensitive material used for full-color display and containing a photopolymerizable composition in a microcapsule), paints, adhesives, and so on.

14 Claims, No Drawings

PHOTOPOLYMERIZABLE COMPOSITION

TECHNICAL FIELD

The present invention relates to a photopolymerizable composition advantageously used for a visible laser recording material, such as a PS (Presensitized Plate) for laser direct plate-making, a dry film resist, a digital proof, a hologram, or the like, a panchromatic sensitive material (e.g., a sensitive material for a color hologram and a sensitive material used for full-color display and containing a photopolymerizable composition in a microcapsule), paints, adhesives, and so on.

BACKGROUND ART

Conventionally, a photopolymerizable composition using a squarylium compound as a sensitizing dye has been known.

Japanese Published Unexamined Patent Application No.48665/1990 discloses a photopolymerizable composition in which a squarylium compound is used as a sensitizing dye and s-triazine is used as a radical generator.

Also, Japanese Published Unexamined Patent Application No.142346/1988 discloses a photopolymerizable composition in which a squarylium compound is used as a sensitizing dye and an adinium salt is used as a radical generator.

Further, Japanese Published Unexamined Patent Application No.17525/1993 discloses a photopolymerizable composition in which a squarylium compound is used as a sensitizing dye and a metal-arene complex is used as a radical generator.

DISCLOSURE OF THE INVENTION

An object of the present invention is to provide a photopolymerizable composition having a high photosensitivity.

The present invention provides the following [1] to [11].

[1] A photopolymerizable composition comprising a metal complex of a squarylium compound, a radical generator, and a compound having at least one ethylenically unsaturated double bond.

[2] The photopolymerizable composition according to the above [1], wherein the squarylium compound is represented by general formula (I)

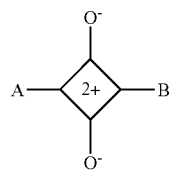

(I)

in which at least one of A and B is represented by general formula (II)

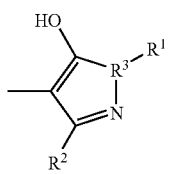

(II)

(wherein $R^1$ and $R^2$ may be the same or different and each denotes an optionally substituted alkyl, an optionally substituted aralkyl, an optionally substituted aryl, or an optionally substituted heterocyclic group; and $R^3$ denotes a nitrogen atom or an oxygen atom, with the proviso that when $R^3$ is an oxygen atom, $R^1$ does not exist)

[3] The photopolymerizable composition according to the above [2], wherein the squarylium compound is the one wherein one of A and B in the formula (I) is represented by general formula (III)

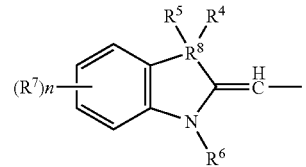

(III)

(wherein $R^4$ and $R^5$ may be the same or different and each denotes a hydrogen atom or an optionally substituted alkyl, an optionally substituted aralkyl, or an optionally substituted aryl group; or when $R^8$ described below is a carbon atom, $R^4$ and $R^5$ may form an alicyclic hydrocarbon ring or a heterocyclic ring together with the adjacent carbon atom; $R^6$ denotes a hydrogen atom or an optionally substituted alkyl, an optionally substituted aralkyl, or an optionally substituted aryl group; $R^7$ denotes a halogen atom, an optionally substituted alkyl, an optionally substituted aralkyl, or an optionally substituted aryl group, a nitro group, a cyano group, or an optionally substituted alkoxy group; n denotes an integer of from 0 to 4; when n is an integer of from 2 to 4, $R^7$'s may be the same or different and two adjacent $R^7$'s and the respective two adjacent carbon atoms may together form an optionally substituted aromatic ring; and $R^8$ denotes a carbon atom, a sulfur atom, a nitrogen atom, or an oxygen atom, with the proviso that when $R^8$ is a sulfur atom or an oxygen atom, $R^4$ and $R^5$ do not exist; and that when $R^8$ is a nitrogen atom, $R^5$ does not exist).

[4] The photopolymerizable composition according to the above [2], wherein the squarylium compound is the one wherein one of A and B in the formula (I) is represented by general formula (IV)

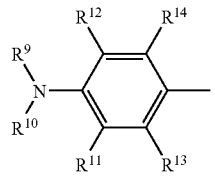

(IV)

(wherein $R^9$ and $R^{10}$ may be the same or different and each denotes a hydrogen atom or an optionally substituted alkyl group; or $R^9$ and $R^{10}$ may form a heterocyclic ring together with the adjacent nitrogen atom; $R^{11}$, $R^{12}$, $R^{13}$, and $R^{14}$ may be the same or different and each denotes a hydrogen atom, an optionally substituted alkyl or an optionally substituted alkoxy group, a hydroxyl group, or a halogen atom; and $R^9$ and $R^{12}$, or $R^{10}$ and $R^{11}$ may form an optionally substituted heterocyclic ring together with the adjacent N—C—C).

[5] The photopolymerizable composition according to any of the above [1] to [4], the metal in the metal complex of a squarylium compound is aluminum, zinc, or beryllium.

[6] A metal complex of a squarylium compound represented by general formula (Ia)

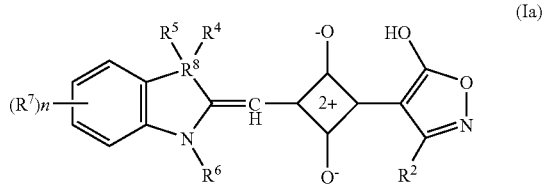

(Ia)

(wherein $R^2$, $R^4$, $R^5$, $R^6$, $R^7$, $R^8$, and n are as defined above, respectively).

[7] The metal complex of a squarylium compound according to the above [6], wherein the metal in the metal complex of a squarylium compound is aluminum, zinc, or beryllium.

[8] A metal complex of a squarylium compound represented by general formula (Ib)

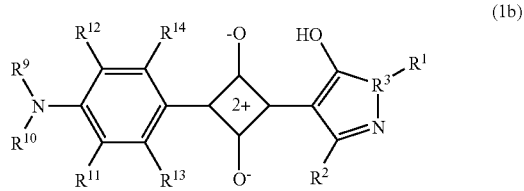

(Ib)

(wherein $R^1$, $R^2$, $R^3$, $R^9$, $R^{10}$, $R^{11}$, $R^{12}$, $R^{13}$, and $R^{14}$ are as defined above, respectively).

[9] The metal complex of a squarylium compound according to the above [8], wherein the metal in the metal complex of a squarylium compound is aluminum, zinc, or beryllium.

[10] A metal complex of a squarylium compound represented by general formula (Ic)

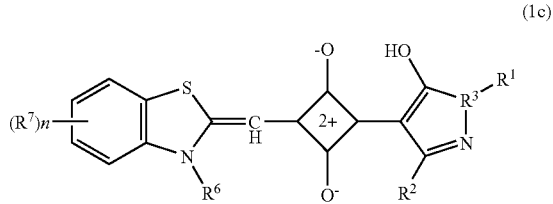

(Ic)

(wherein $R^1$, $R^2$, $R^3$, $R^6$, $R^7$, and n are as defined above, respectively).

[11] The metal complex of a squarylium compound according to the above [10], wherein the metal in the metal complex of a squarylium compound is aluminum, zinc, or beryllium.

In the above-described definition of each group in the general formulae, an alkyl portion of the alkyl group and the alkoxy group is, e.g., any of linear or branched alkyl groups having the carbon number of 1 to 6 or cyclic alkyl groups having the carbon number of 3 to 8. Examples of those alkyl portions include a methyl group, an ethyl group, a propyl group, an isopropyl group, a butyl group, an isobutyl group, a sec-butyl group, a tert-butyl group, a pentyl group, an isopentyl group, a 1-methylbutyl group, a 2-methylbutyl group, a tert-pentyl group, a hexyl group, a cyclopropyl group, a cyclobutyl group, a cyclopentyl group, a cyclohexyl group, a cycloheptyl group, and a cyclooctyl group.

The aralkyl group is, e.g., any of aralkyl groups having the carbon number of 7 to 15. Examples of those aralkyl groups include a benzyl group, a phenethyl group, a phenylpropyl group, and a naphthylmethyl group.

The aryl group is, e.g., any of aryl groups having the carbon number of 6 to 14. Examples of those aryl groups include a phenyl group, a naphthyl group, an anthryl group, and an azulenyl group.

Examples of the halogen atom include a chlorine atom, a bromine atom, a fluorine atom, and an iodine atom.

The aromatic ring which two adjacent $R^7$'s form together with the respective two adjacent carbon atoms is, e.g., a benzene ring.

The heterocyclic ring in the heterocyclic group and the heterocyclic ring, which $R^4$ and $R^5$ form together with the adjacent carbon atom, are each, e.g., any of 5- or 6-membered monocyclic aromatic or aliphatic heterocyclic rings containing at least one atom selected from a nitrogen atom, an oxygen atom and a sulfur atom, or fused aromatic or aliphatic heterocyclic rings which are bycyclic or tricyclic with 3- to 8-membered rings condensed and contain at least one atom selected from a nitrogen atom, an oxygen atom and a sulfur atom. Examples of those heterocyclic rings include a pyridine ring, a pyradine ring, a pyrimidine ring, a pyridazine ring, a quinoline ring, an isoquinoline ring, a phthalazine ring, a quinazoline ring, a quinoxaline ring, a naphthyridine ring, a cinnoline ring, a pyrrole ring, a pyrazole ring, an imidazole ring, a triazole ring, a tetrazole ring, a thiophene ring, a furan ring, a thiazole ring, an oxazole ring, an indole ring, an isoindole ring, an indazole ring, a benzoimidazole ring, a benzotriazole ring, a benzothiazole ring, a benzoxazole ring, a purine ring, a carbazole ring, a pyrrolidine ring, a piperidine ring, a piperazine ring, a morpholine ring, a thiomorpholine ring, a homopiperidine ring, a homopiperazine ring, a tetrahydropyridine ring, a tetrahydroquinoline ring, a tetrahydroisoquinoline ring, a tetrahydrofuran ring, a tetrahydropyrane ring, a dihydrobenzofuran ring, and a tetrahydrocarbazole ring.

The alicyclic hydrocarbon ring which $R^4$ and $R^5$ form together with the adjacent carbon atom, is, e.g., any of saturated or unsaturated ones having the carbon number of 3 to 8. Examples of those alicyclic hydrocarbon rings include a cyclopropane ring, a cyclobutane ring, a cyclopentane ring, a cyclohexane ring, a cycloheptane ring, a cyclooctane ring, a cyclopentene ring, a 1,3-cyclopentadiene ring, a cyclohexene ring, and a cyclohexadiene ring.

The heterocyclic ring which $R^9$ and $R^{12}$, or $R^{10}$ and $R^{11}$ form together with the adjacent N—C—C, and the heterocyclic ring which $R^9$ and $R^{10}$ form together with the adjacent nitrogen atom, are each, e.g., any of 5- or 6-membered monocyclic heterocyclic rings containing at least one nitrogen atom (the monocyclic heterocyclic ring may contain another nitrogen atom, an oxygen atom or a sulfur atom), or fused heterocyclic rings which are bycyclic or tricyclic with 3- to 8-membered rings condensed and contain at least one nitrogen atom (the fused heterocyclic ring may contain another nitrogen atom, an oxygen atom or a sulfur atom). Examples of those heterocyclic rings include a pyrrolidine ring, a piperidine ring, a piperazine ring, a morpholine ring, a thiomorpholine ring, a homopiperidine ring, a homopiperazine ring, a tetrahydropyridine ring, a tetrahydroquinoline ring, and a tetrahydroisoquinoline ring.

The substituent(s) for the aralkyl group, the aryl group, the aromatic ring, the heterocyclic group, and the heterocyclic ring which $R^9$ and $R^{12}$, or $R^{10}$ and $R^{11}$ form together with the adjacent N—C—C, is (are), e.g., one to five substituents being the same or different from each other. Examples of those substituents include a hydroxyl group, a carboxyl group, a halogen atom, an alkyl group, an alkyl-substituted or unsubstituted amino group, an alkoxy group, and a nitro group. The halogen atom, the alkyl group, and the alkoxy group have the same meanings as defined above, respectively, and an alkyl portion of the alkyl-substituted amino group is the same as the alkyl group defined above.

The substituent(s) for the alkyl group and the alkoxy group is (are), e.g., one to three substituents being the same or different from each other. Examples of those substituents include a hydroxyl group, a carboxyl group, a halogen atom, and an alkoxy group. The halogen atom and the alkoxy group have the same meanings as defined above, respectively.

The metal in the metal complex of a squarylium compound is not limited to a particular one so long as it forms a complex together with the squarylium compound. Examples of the metal include aluminum, zinc, beryllium, copper, iron, nickel, chromium, cobalt, manganese, iridium, vanadium, and titanium. Among them, aluminum, zinc, or beryllium is preferred.

In the metal complex of a squarylium compound, the coordination number of the squarylium compound is preferably two or three.

A method of producing the metal complex of the squarylium compound will be described below.

squalirium compound

metal complex of squalirium compound (wherein $Q^{q+}$ represents a metal ion having the coordinating property, Q represents a metal, and q represents the valence of an ion produced from the metal).

The metal complex of the squarylium compound is obtained by reacting a squarylium compound and a material providing a metal ion having the coordinating property (i.e., a material providing $Q^{q+}$) in a solvent the presence of an acid, at a temperature from the room temperature to 120° C. for 5 minutes to 15 hours. The material providing $Q^{q+}$ is preferably used in such an amount that a ratio of the mol number of the squarylium compound to the mol number of the material providing $Q^{q+} \times q$ is in the range of 1:0.5 to 2.

Examples of the material providing $Q^{q+}$ include aluminum tris(acetylacetonate), aluminum tris(ethylacetoacetate), aluminum triisopropoxide, aluminum tri-sec-butoxide, aluminum triethoxide, aluminum chloride, zinc acetate, zinc chloride, beryllium sulfate, copper chloride, copper acetate, and nickel acetate.

Examples of the acid includes organic acids, such as acetic acid, propionic acid, butyric acid, isobutyric acid, valeric acid, isovaleric acid and p-toluene sulfonic acid, and inorganic acids, such as hydrochloric acid, sulfuric acid and phosphoric acid. The amount of the acid used is preferably in the range of 0.1 to 2 mol for 1 mol of the squarylium compound.

Examples of the solvent include a halogen-based solvent, such as chloroform and dichloromethane, an aromatic-based solvent, such as toluene and xylene, an ether-based solvent, such as tetrahydrofuran and methyl-tert-butylether, and an ester-based solvent, such as an ethyl acetate. The amount of the solvent used is preferably in the range of 1 to 500 weight parts for 1 weight part of the squarylium compound.

Of the squarylium compounds used as starting materials for the metal complex of the squarylium compound, the squarylium compound defined by the general formula (I) with A and B being the same group can be produced in accordance with or with reference to the methods described in, for example, "OXOCARBONS", p 191, 1980, ACADEMIC PRESS. Also, the squarylium compound defined by the general formula (I) with A and B being different groups can be produced in accordance with or with reference to the methods described in, for example, "SENRYO TO YAKUHIN (DYES AND PHARMACEUTICALS)", vol. 42, No. 9, p 10, 1997 and WO 01/44233.

Preferred practical examples of the metal complex of the squarylium compound used in the photopolymerizable composition of the present invention are listed in Table 1 given below. Note that, in Table 1, "Ph" denotes a phenyl group, "Me" denotes a methyl group, "Et" denotes an ethyl group, "Pr" denotes a propyl group, and "'Pr" denotes an isopropyl group.

TABLE 1

Practical Examples of Metal Complex of Squarylium Compound

| Squarylium Compound | $Q^{q+}$ | Metal Complex of Squarylium Compound |
|---|---|---|
| 1-1 | $Al^{3+}$ | 1-2 |

TABLE 1-continued

Practical Examples of Metal Complex of Squarylium Compound

| Squarylium Compound | $Q^{q+}$ | Metal Complex of Squarylium Compound |
|---|---|---|
| 2-1 | $Al^{3+}$ | 2-2 |
| 3-1 | $Al^{3+}$ | 3-2 |
| 4-1 | $Al^{3+}$ | 4-2 |
| 5-1 | $Al^{3+}$ | 5-2 |

TABLE 1-continued

Practical Examples of Metal Complex of Squarylium Compound

| Squarylium Compound | $Q^{q+}$ | Metal Complex of Squarylium Compound |
|---|---|---|
| 6-1 | $Al^{3+}$ | 6-2 |
| 7-1 | $Al^{3+}$ | 7-2 |
| 8-1 | $Be^{2+}$ | 8-2 |
| 9-1 | $Al^{3+}$ | 9-2 |

TABLE 1-continued

Practical Examples of Metal Complex of Squarylium Compound

| Squarylium Compound | $Q^{q+}$ | Metal Complex of Squarylium Compound |
|---|---|---|
| 10-1 | $Be^{2+}$ | 10-2 |
| 11-1 | $Zn^{2+}$ | 11-2 |
| 12-1 | $Al^{3+}$ | 12-2 |

The photopolymerizable composition of the present invention will be described below.

The photopolymerizable composition of the present invention can be obtained by mixing a metal complex of a squarylium compound, a radical generator, and a compound having at least one ethylenically unsaturated double bond along with, as required, a binder or additives (such as a thermal polymerization inhibitor, a plasticizer, or an organic solvent). The order and method of adding those components are not limited to particular ones.

Examples of the radical generator include s-triazine compounds having at least one trihalomethyl group (such as 2,4,6-tris(trichloromethyl)-s-triazine, 2-(4-methoxyphenyl)-4,6-bis(trichloromethyl)-s-triazine, and 2-(4-methoxy-1-naphthalenyl)-4,6-bis(trichloromethyl)-s-triazine), organic peroxides (such as 3,3'4,4'-tetrakis(tert-butyldioxycarbonyl) benzophenone), N-phenylglycines (such as N-phenylglycine, p-chloro-N-phenylglycine, and m-methyl-N-phenylglycine), aromatic sulfonyl halide compounds (such as benzenesulfonyl chloride and p-toluenesulfonyl chloride), imidazole dimers (such as 2,2'-bis(o-chlorophenyl)-4,4',5,5'-tetraphenylbiimidazole), metal-arene complexes (such as ($\eta^6$-benzene) ($\eta^5$-cyclopentadienyl)iron(II)hexafluorophosphate and fluoroaryltitanocene), diaryliodonium salts (such as 8-anilinonaphthalene-1-sulfonic diphenyliodonium salt), triarylsulfonium salts, branched polyethylene imines, alkyl or aryl sulfonium salts (such as tetrabutylammonium triphenylbutyl borate), aromatic ketones (such as thioxanthone), acetophenones (such as benzoinether and benzyldimethylketal), diketones, acyl oxime esters, and sulfur compounds (thiols and disulfides). The amount of the radical generator used is preferably in the range of 0.1 to 100 weight parts, more preferably in the range of 1 to 50 weight parts, for 1 weight part of the metal complex of the squarylium compound.

The compound having at least one ethylenically unsaturated double bond is not limited to a particular one so long as the compound addition-polymerizes induced by a radical generated upon light-exposure of the photopolymerizable composition of the present invention. Examples of the compound having at least one ethylenically unsaturdouble bond include unsaturated carboxylic acids, such as acrylic acid, methacrylic acid, itaconic acid, crotonic acid, and maleic acid;

esters derived from an unsaturated carboxylic acid and a monohydroxy compound, e.g., (meth)acrylic acid esters, such as methyl (meth)acrylate, butyl (meth)acrylate, 2-phenoxyethyl acrylate, p-chlorophenyl (meth)acrylate, 2-(1-naphthyloxy)ethyl (meth)acrylate, o-biphenyl (meth)acrylate, pentachlorophenyl (meth)acrylate, 2,4,6-tribromophenyl (meth)acrylate, 2-naphthyl (meth)acrylate, 2-(2-naphtyloxy)ethyl (meth)acrylate, trifluoroethyl (meth)acrylate, tetrafluoropropyl (meth)acrylate, dibromopropyl (meth)acrylate, ethyl-2-chloro (meth)acrylate, and tetrahydrofurfuryl (meth)acrylate;

esters derived from an unsaturated carboxylic acid and an aliphatic polyhydroxy compound, such as ethyleneglycol di(meth)acrylate, triethyleneglycol di(meth)acrylate, tetraethyleneglycol di(meth)acrylate, propyleneglycol di(meth)acrylate, neopentylglycol di(meth)acrylate, 1,3-butanediol di(meth)acrylate, 1,4-cyclohexanediol di(meth)acrylate, hexanediol di(meth)acrylate, trimethylolpropane tri(meth)acrylate, trimethylolethane tri(meth)acrylate, trimethylolpropane tris((meth)acryloyloxypropyl) ether, pentaerythritol di(meth)acrylate, pentaerythritol tri(meth)acrylate, pentaerythritol tetra(meth)acrylate, dipentaerythritol di(meth)acrylate, dipentaerythritol tri(meth)acrylate, dipentaerythritol tetra(meth)acrylate, dipentaerythritol penta(meth)acrylate, dipentaerythritol hexa(meth)acrylate, glycerol (meth)acrylate, sorbitol tri(meth)acrylate, sorbitol tetra (meth)acrylate, sorbitol penta(meth)acrylate, sorbitol hexa (meth)acrylate, an itaconic acid ester, a crotonic acid ester, and a maleic acid ester;

esters derived from an unsaturated carboxylic acid and an aromatic polyhydroxy compound, such as hydroquinone di(meth)acrylate, resolcine di(meth)acrylate, pyrogallol tri(meth)acrylate, ethyleneoxide denatured bisphenol A di(meth)acrylate, and tris(β-(meth)acryloyloxyethyl)-s-cyanurate;

polyesters obtained by employing, as starting materials, an unsaturated carboxylic acid, a polyhydric carboxylic acid and a polyhydroxy compound, such as a polyester obtained by employing, as starting materials, (meth) acrylic acid, phthalic acid and ethylene glycol, a polyester obtained by employing, as starting materials, (meth)acrylic acid, maleic acid and diethylene glycol, a polyester obtained by employing, as starting materials, (meth)acrylic acid, terephthalic acid and pentaerythritol, a polyester obtained by employing, as starting materials, (meth)acrylic acid, adipic acid, butanediol and glycerin, and a polyester obtained by employing, as starting materials, (meth)acrylic acid, trimellitic acid and diethylene glycol;

polymers obtained by reacting, e.g., polyvinyl alcohol, poly(2-hydroxyethyl methacrylate), an epoxy resin, a phenoxy resin polyepichlorohydrine, or the like with an unsaturated carboxylic acid, such as acrylic acid, methacrylic acid or crotonic acid, and the like; acryl amides such as ethylene bisacrylamide, N-vinylcarbazole, N-vinylpyrrolidone, and so on.

The term "methyl (meth)acrylate" used in the above description means methyl acrylate and methyl methacrylate. Similar expressions with regards to other components also have the same meaning. The amount of the compound having at least one ethylenically unsaturated double bond is preferably in the range of 2 to 1000 weight parts, more preferably in the range of 20 to 200 weight parts, for 1 weight part of the metal complex of the squarylium compound.

The binder is, for example, poly(meth)acrylic acid ester or a partial hydrolysate thereof, polyvinyl acetate or a partial hydrolysate thereof, a copolymer of vinylacetate and ethylene or a partial hydrolysate thereof, polystyrene, polyvinyl formal, polyvinyl butyral, polychloroprene, polyvinyl chloride, chlorinated polyethylene, chlorinated polypropylene, phenol novolac resin or cresol novolac resin, polyvinyl phenol, a copolymer of vinylphenol and methacrylic acid ester, polyethylene oxide, polymethylisopropenyl ketone, a copolymer of methacrylic acid ester and phenylisopropenyl ketone, polyurethane, polyamide, polycarbonate, polyethylene terephthalate, polybutylene terephthalate, acetylcellulose, acetylbutylcellulose, nitrocellulose, polyvinylcarbazole or a derivative thereof, a copolymer of vinylcarbazole and styrene, a copolymer of vinylcarbazole and (meth) acrylic aid ester, polyvinylpyrrolidone or a derivative thereof, a copolymer of vinylpyrrolidone and styrene, a copolymer of vinylpyrrolidone and (meth)acrylic aid ester, a copolymer of styrene and maleic acid (monoester), or a copolymer produced by selecting, as starting materials, two or more of copolymerizable monomers, such as (meth) acrylic acid ester, (meth)acrylic acid, (anhydrous) maleic acid, acrylonitrile, acrylic amide, styrene, vinyl acetate, vinyl chloride, vinylidene chloride, butadiene, isoprene, and chloroprene. The amount of the binder used is preferably in the range of 10 to 1000 weight parts, more preferably in the range of 60 to 200 weight parts, for 100 weight parts of the compound having at least one ethylenically unsaturated double bond.

The thermal polymerization inhibitor is, for example, p-(tert-butyl)-catechol, hydroquinone, or chloranil. The content of the thermal polymerization inhibitor in the photopolymerizable composition of the present invention is preferably in the range of 0.000001 to 0.1 percent by weight and more preferably in the range of 0.000001 to 0.05 percent by weight.

The plasticizer is, for example, diethylhexyl phthalate, diisobutyl phthalate, tricresyl phosphate, diethylhexyl sebacate, or diethylhexyl adipate. The content of the plasticizer in the photopolymerizable composition of the present invention is preferably in the range of 0.001 to 20 percent by weight and more preferably in the range of 0.01 to 5 percent by weight.

Examples of the organic solvent include ethers such as dimethoxyethane, methoxyethoxyethane, tetrahydrofuran and dioxane, ketones such as acetone, methylethylketone, methylisobutylketone and cyclohexanone, aromatic hydrocarbons such as benzene, toluene, xylene and monochlorobenzene, and aliphatic hydrocarbons such as hexane and cyclohexane. The content of the organic solvent in the photopolymerizable composition of the present invention is preferably in the range of 1 to 90 percent by weight.

The photopolymerizable composition of the present invention is advantageously used as a visible laser recording material, such as a PS for laser direct plate-making, a dry film resist, a digital proof, a hologram, etc., a panchromatic sensitive material (e.g., a sensitive material for a color hologram and a sensitive material used for full-color display and containing the photopolymerizable composition in a microcapsule), paints, adhesives, and so on.

When the photopolymerizable composition of the present invention is used as a visible laser recording material in a hologram, etc., a solution containing the photopolymerizable composition of the present invention (i.e., a sensitive liquid) is coated on, e.g., an aluminum plate by, for example, spin coating, and a laser beam is illuminated to the aluminum plate. Subsequently, the exposed aluminum plate is developed by using an aqueous solution of tetramethylammonium hydroxide or the like as a developer, and is washed with water, followed by drying. As a result, the visible laser recording material, such as a hologram, can be obtained.

The photopolymerizable composition of the present invention has superior properties in photosensitivity, etc.

BEST MODE FOR CARRYING OUT THE INVENTION

The present invention will be described in more detail below in connection with Examples and Reference Examples.

REFERENCE EXAMPLE 1

8.95 g of 3,4-dimethoxy-3-cyclobutene-1,2-dione and 12.74 g of 1-phenyl-3-propylpyrazoline-5-on were dissolved in 150 ml of methanol. After adding 8.71 g of potassium carbonate, a resulting mixture was stirred at 25° C. for 1 hour. After the reaction, a precipitate was obtained through filtering. The solid thus obtained was added to a solution of 3 g of potassium carbonate and 130 ml of water, and then the mixture was stirred under reaction at 50° C. for 5 hours. After the reaction, 100 ml of a 1-mol/L aqueous solution of hydrochloric acid was added and an insoluble was obtained through filtering the solid thus obtained was added to the mixture of 90 ml of n-butanol, 45 ml of toluene, and 9.30 g of 5-chloro-1,3,3-trimethyl-2-methyleneindoline, and the mixture was stirred under reaction at 110° C. for 5 hours. After adding 100 ml of methanol, a resulting mixture was stirred under reaction at 80° C. for 1 hour. A precipitate was obtained through filtering, whereby a compound 1-1 was obtained. The compound 1-1 was added to the mixture of 90 ml of ethyl acetate, 17.5 ml of acetic acid, and 4.97 g of aluminum tris(ethylacetoacetate), and then the mixture was stirred under reaction at 50° C. for 2 hours. An insoluble was obtained through filtering, whereby 13.75 g of a compound 1-2 was obtained.

Elemental Analysis ($C_{84}H_{75}AlCl_3N_9O_9$): Theoretical Value (%) C, 67.81, H 5.08, N 8.47 Measured Value (%) C 67.71, H 4.89, N 8.46 $^1$H NMRδ (CDCl$_3$) ppm:0.96 (3H, t, J=7.3 Hz), 1.02 (3H, t, J=7.4 Hz), 1.04 (3H, t, J=7.3 Hz), 1.26-1.81 (24H, m), 2.81-3.12 (6H, m), 3.40 (3H, s), 3.44 (6H, m), 5.63 (2H, m), 5.70 (1H, s), 6.86-6.88 (3H, m), 7.02-7.26 (15H, m), 7.83-7.97 (6H, m).

IR(KBr) cm$^{-1}$:2958, 1753, 1633, 1081, 794.

REFERENCE EXAMPLE 2

A compound 2-2 was obtained through the similar process as that in Reference Example 1 except that 10.97 g of 1-phenyl-3-methylpyrazoline-5-on was used instead of 1-phenyl-3-propylpyrazoline-5-on and 7.8 g of 1,3,3-trimethyl-2-methyleneindoline was used instead of 5-chloro-1,3,3-trimethyl-2-methyleneindoline.

Elemental Analysis ($C_{78}H_{66}AlN_9O_9$) Theoretical Value (%) C 72.04, H 5.12, N 9.69 Measured Value (%) C 71.95, H 5.11, N 9.42 $^1$H NMRδ (CDCl$_3$) ppm: 1.60 (18H, m), 2.42 (3H, s), 2.52 (3H, s), 2.64 (3H, s), 3.48 (6H, m), 3.58 (3H, m), 5.65 (2H, m), 5.74 (1H, s), 6.97-7.30 (21H, m), 7.82-8.01 (6H, m). IR(KBr) cm$^{-1}$:2964, 1763, 1601, 1095, 798.

REFERENCE EXAMPLE 3

A compound 3-2 was obtained through the similar process as that in Reference Example 1 except that 8.83 g of 1-methyl-3-isopropylpyrazoline-5-on was used instead of 1-phenyl-3-propylpyrazoline-5-on.

Elemental Analysis ($C_{69}H_{69}AlCl_3N_9O_9$): Theoretical Value (%) C 63.67, H 5.34, N 9.68 Measured Value (%) C 63.67, H 5.55, N 9.56 $^1$H NMRδ (CDCl$_3$) ppm: 1.24-1.31 (18H, m), 1.57-1.88 (18H, m), 3.13 (9H, m), 3.45 (3H, m), 3.74-3.81 (3H, m), 5.71 (2H, m), 6.85-6.87 (3H, m), 7.17-7.27 (6H, m). IR(KBr) cm$^{-1}$:2966, 1763, 1610, 1166, 798.

REFERENCE EXAMPLE 4

A compound 4-2 was obtained through the similar process as that in Reference Example 1 except that 9.15 g of 5-methoxy-1,3,3-trimethyl-2-methyleneindoline was used instead of 5-chloro-1,3,3-trimethyl-2-methyleneindoline.

Elemental Analysis ($C_{87}H_{84}AlN_9O_{12}$): Theoretical Value (%) C 70.86, H 5.74, N 8.55 Measured Value (%) C 70.67, H 5.89, N 8.55 $^1$H NMRδ (CDCl$_3$) ppm: 1.02 (9H, m), 1.24-1.76 (24H, m), 2.80-3.12 (6H, m), 3.44-3.48 (9H, m), 3.67 (9H, m), 5.65 (3H, m), 6.57-6.90 (9H, m), 6.98-7.01 (3H, m), 7.10-7.18 (6H, m), 7.84-8.00 (6H, m). IR(KBr) cm$^{-1}$:2958, 1763, 1601, 1462, 1446, 1423, 1306, 1281, 1240, 1097, 1072, 1016.

REFERENCE EXAMPLE 5

A compound 8-2 (9.84 g) was obtained through the similar process as that in Reference Example 1 except that 1700 ml of ethanol, 510 ml of water, and 3.11 g of beryllium sulfate 4-hydrates were used instead of ethyl acetate, acetic acid, and aluminum tris(ethylacetoacetate), respectively, and the reaction was performed with reflux under heating for 5 hours instead of reacting the mixture at 50° C. for 2 hours.

Elemental Analysis ($C_{56}H_{50}BeCl_2N_6O_6$): Theoretical Value (%) C 68.43, H 5.13, N 8.55 Measured Value (%) C 68.19, H 5.19, N 8.44 Maximum Absorption Wavelength (chloroform) λmax: 578 nm Mass Spectrum (FAB): m/z=981

EXAMPLE 1

20 ml of n-butanol and 10 ml of toluene were added to 1.22 g of 3-hydroxy-4-(1,3,3-trimethyl-5-chloroindoline-2-ylidenemethyl)-3-cyclobutene-1,2-dione and 0.64 g of 5-hydroxy-3-phenylisoxzole, and then heated at 110° C. for 10 hours. Thereafter, a precipitate was obtained through filtering. A solid thus obtained was refined with a column chromatography (silica gel, developing solution; chloroform/methanol), whereby 0.67 g of a compound 9-1 was obtained.

The compound 9-1 thus obtained was added with 0.20 g of aluminum tris(ethylacetoacetate), 0.1 g of acetic acid, and 67 ml of acetone, and then left under reaction at 50° C. for 10 hours. After condensing a solution after the reaction, a condensate was refined with a column chromatography (silica gel, developing solution; chloroform/methanol), whereby 0.04 g of a compound 9-2 was obtained.

$^1$H NMRδ (CDCl$_3$) ppm: 1.21-1.80 (18H, m), 3.12-3.77 (9H, m), 5.52-5.88 (3H, m), 6.82-7.78 (24H, m)

EXAMPLE 2

A compound 10-1 (15.3 g) was obtained by employing 330 ml of n-butanol, 330 ml of toluene, 5.81 g of quinoline, and 13.73 g of 1-ethyl-2-methylbenzothiazolium iodide instead of 90 ml of n-butanol, 45 ml of toluene, and 9.30 g of 5-chloro-1,3,3-trimethyl-2-methyleneindoline which were employed in Reference Example 1, subjecting the mixture under the refluxing condition for 9 hours, and filtering the mixture. The compound 10-1 thus obtained was added to 1700 ml of ethanol, 510 ml of water, and 3.70 g of beryllium sulfate 4-hydrates. After subjecting the mixture under the refluxing condition for 5 hours, an insoluble was obtained through filtering, whereby a compound 10-2 (13.43 g) was obtained.

Elemental Analysis ($C_{52}H_{44}BeN_6O_6S_2$): Theoretical Value (%) C 67.73, H 4.81, N 9.11, S 6.95 Measured Value (%) C 67.57, H 4.90, N 9.12, S 6.85 Maximum Absorption Wavelength (chloroform) λmax: 589 nm Mass Spectrum (FAB): m/z=921

EXAMPLE 3

A compound 11-2 (14.39 g) was obtained through the similar process as that in Example 2 except for employing 1700 ml of ethanol and 4.26 g of zinc acetate 2-hydrates instead of ethanol, water and beryllium sulfate 4-hydrates, and subjecting the mixture to reflux under heating for 7 hours instead of reflux under heating for 9 hours.

Elemental Analysis ($C_{52}H_{44}N_6O_6S_2Zn$): Theoretical Value (%) C 63.83, H 4.53, N 8.59, S 6.55 Measured Value (%) C 63.64, H 4.65, N 8.53, S 6.46 $^1$H NMRδ ($CDCl_3$) ppm: 0.76 (6H, t), 0.85 (6H, t), 1.26-1.35 (4H, m), 2.04-2.11 (2H, m), 3.02-3.09 (2H, m), 3.31-3.40 (2H, m), 4.35-4.43 (2H, m), 6.69 (2H, d), 6.75 (2H, s), 6.81 (2H, t), 6.91 (4H, t), 7.33-7.41 (4H, m), 7.64 (2H, d), 7.82 (4H, d).

Maximum Absorption Wavelength (chloroform) λmax: 504, 566, 693 nm

Mass Spectrum (FAB): m/z=976

EXAMPLE 4

A mixture of 9.89 g of 3,4-dichloro-3-cyclobutene-1,2-dione, 9.94 g of N,N-diethylaniline, 5.27 g of pyridine, and 175 ml of dichloromethane was stirred at the room temperature for 4.5 hours. A resulting reaction mixture was refined with a silica column chromatography (developing solution; dichloromethane). A resulting portion was evaporated to obtain a solid. The solid was added to 30 ml of acetic acid and 20 ml of water, and then subjected to reflux under heating for 50 minutes. Thereafter, a precipitate was obtained through filtering. 8.42 g of a solid thus obtained was added with 84 ml of n-butanol, 42 ml of toluene, and 7.07 g of 1-phenyl-3-propylpyrazoline-5-on. After refluxing the mixture for 4.5 hours, a precipitate was obtained through filtering, whereby 12.27 g of a compound 12-1 was obtained. The compound thus obtained was added with 1200 ml of isopropyl alcohol, 4.9 ml of acetic acid, and 5.66 g of aluminum tris(ethylacetoacetate), and then subjected to reflux under heating for 6 hours. An insoluble was obtained through filtering, whereby a compound 12-2 (9.74 g) was obtained.

Elemental Analysis ($C_{78}H_{78}AlN_9O_9$): Theoretical Value (%) C 71.38, H 5.99, N 9.60 Measured Value (%) C 71.70, H 5.80, N 9.35 $^1$H NMRδ ($CDCl_3$) ppm: 0.96 (9H, t), 1.20 (18H, t), 1.52-1.66 (6H, m), 2.69-2.76 (3H, m), 2.92-2.99 (3H, m), 3.43 (12H, q), 6.60 (6H, d), 7.02-7.10 (9H, m), 7.88-8.10 (12H, m) Maximum Absorption Wavelength (chloroform) λmax: 544, 579 nm Mass Spectrum (FAB): m/z=1311

EXAMPLE 5

100 weight parts of pentaerythritol triacryrate, 100 weight parts of a polymethacrylic acid ester polymer [material composition ratio, methacrylic acid: benzyl methacrylate=30%:70% (mol ratio); mean molecular weight 31000], 3.7 weight parts of 2,4,6-tris(trichloromethyl)-s-triazine, and 0.6 weight part of the metal complex (compound 1-2 or 4-2) of the squarylium compound or the squarylium compound (compound 1-1 or 4-1) were all dissolved in 800 weight parts of cyclohexane, and a photopolymerizable composition was obtained. The photopolymerizable composition was coated on an aluminum plate under rotation, which had been subjected to sand dressing and the anodic oxidation process. By drying the coated aluminum plate with warm air, a photosensitive layer with an average film thickness of 1 to 1.2 μm was obtained. A stepped tablet was positioned on the thus-obtained photosensitive layer in a close contact relation, and a light with wavelength of not shorter than 560 nm was irragiated to the photosensitive layer from a super-high-pressure mercury lamp of 450 W for 1 minute. The light was passed through an O-56 filter to remove light with wavelength of not longer than 560 nm (light intensity: 12.1 mJ/cm$^2$·s). Subsequently, the exposed aluminum plate was developed by using an aqueous solution of 2.38 percent by weight of tetramethylammonium hydroxide as a developer, and was washed with water, followed by drying. Then, from a maximum density step (hardened step number) in which a high molecular film of the photosensitive layer remained without being dissolved, the amount of energy required for hardening was determined as sensitivity. The determined results are shown in Table 2 given below.

TABLE 2

| Sensitivity of Squarylium Compound | | Sensitivity of Metal Complex of Squarylium Compound | |
|---|---|---|---|
| Squarylium Compound | Sensitivity (mJ/cm$^2$) | Metal Complex of Squarylium Compound | Sensitivity (mJ/cm$^2$) |
| 1-1 | 910 | 1-2 | 81 |
| 4-1 | 448 | 4-2 | 58 |

INDUSTRIAL APPLICABILITY

The present invention provides a photopolymerizable composition having a high photosensitivity. The photopolymerizable composition of the present invention is advantageously used for a visible laser recording material such as a PS (Presensitized Plate) for laser direct plate-making, a dry film resist, a digital proof, a hologram, or the like, a panchromatic sensitive material (e.g., a sensitive material for a color hologram and a sensitive material used for full-color display and containing a photopolymerizable composition in a microcapsule), paints, adhesives, and so on.

What is claimed is:

1. A photopolymerizable composition comprising a metal complex of a squarylium compound, a radical generator, and a compound having at least one ethylenically unsaturated double bond, wherein the squarylium compound is represented by formula (I)

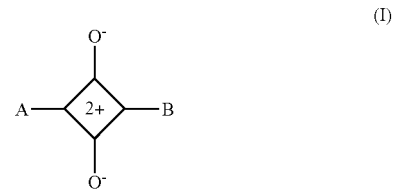

in which at least one of A and B is represented by formula (II)

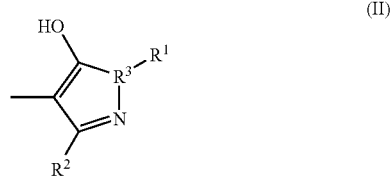

(wherein $R^1$ and $R^2$ independently represent an optionally substituted alkyl, an optionally substituted aralkyl, an optionally substituted aryl, or an optionally substituted heterocyclic group; and $R^3$ represents a nitrogen atom or an oxygen atom, with the proviso that when $R^3$ is an oxygen atom, $R^1$ does not exist), and wherein the metal in the metal complex is aluminum or beryllium.

2. The photopolymerizable composition according to claim 1, wherein one of A and B in formula (I) is represented by formula (III)

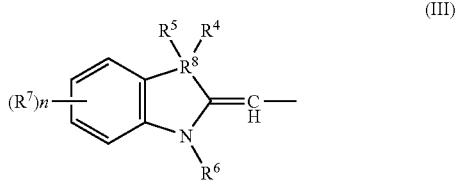

(wherein $R^4$ and $R^5$ independently represent a hydrogen atom or an optionally substituted alkyl, an optionally substituted aralkyl, or an optionally substituted aryl group; or when $R^8$ is a carbon atom, $R^4$ and $R^5$ may form an alicyclic hydrocarbon ring or a heterocyclic ring together with the adjacent carbon atom;

$R^6$ represents a hydrogen atom or an optionally substituted alkyl, an optionally substituted aralkyl, or an optionally substituted aryl group;

all $R^7$ are independently selected from the group consisting of a halogen atom, an optionally substituted alkyl, an optionally substituted aralkyl, or an optionally substituted aryl group, a nitro group, a cyano group, and an optionally substituted alkoxy group; n denotes an integer of from 0 to 4; and when n is an integer of from 2 to 4, two adjacent $R^7$'s and the respective two adjacent carbon atoms may together form an optionally substituted aromatic ring; and $R^8$ denotes a carbon atom, a sulfur atom, a nitrogen atom, or an oxygen atom, with the proviso that when $R^8$ is a sulfur atom or an oxygen atom, $R^4$ and $R^5$ do not exist; and that when $R^8$ is a nitrogen atom, $R^5$ does not exist).

3. The photopolymerizable composition according to claim 1, wherein one of A and B in formula (I) is represented by formula (IV)

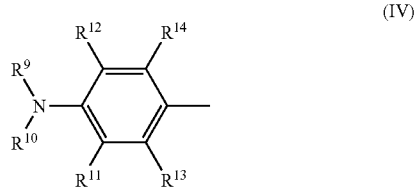

(wherein $R^9$ and $R^{10}$ independently represent a hydrogen atom or an optionally substituted alkyl group; or $R^9$ and $R^{10}$ may form a heterocyclic ring together with the adjacent nitrogen atom; and $R^{11}$, $R^{12}$, $R^{13}$, and $R^{14}$ independently represent a hydrogen atom, an optionally substituted alkyl or an optionally substituted alkoxy group, a hydroxyl group, or a halogen atom; and $R^9$ and $R^{12}$, or $R^{10}$ and $R^{11}$ may form an optionally substituted heterocyclic ring together with the adjacent N—C—C).

4. The photopolymerizable composition according to any of claims 1 to 3, wherein the metal is aluminum.

5. The photopolymerizable composition according to claim 4, wherein the compound with at least one ethylenically unsaturated double bond is an unsaturated carboxylic acid or derivative thereof contained in the amount of 20 to 200 weight parts per part of the metal squarylium complex.

6. The photopolymerizable composition according to claim 5, wherein the radical generator is an S-triazine compound, an organic peroxide, N-phenylglycine, aromatic sulfonyl halide, imidazole dimer, metal-arene complex, di or triarylsulfonium salt, branched polyethylene imine, alkyl or aryl sulfonium salt, aromatic ketone, acetophenone, diketone, acyl oxime ester or sulfur compound contained in the amount of 0.1 to 50 weight parts per part of the metal squarylium complex.

7. The photopolymerizable composition according to any of claims 1 to 3, wherein the compound with at least one ethylenically unsaturated double bond is an unsaturated carboxylic acid or derivative thereof contained in the amount of 20 to 200 weight parts per part of the metal squarylium complex.

8. The photopolymerizable composition according to claim 7, wherein the radical generator is an S-triazine compound, an organic peroxide, N-phenylglycine, aromatic sulfonyl halide, imidazole dimer, metal-arene complex, di or triarylsulfonium salt, branched polyethylene imine, alkyl or aryl sulfonium salt, aromatic ketone, acetophenone, diketone, acyl oxime ester or sulfur compound contained in the amount of 0.1 to 50 weight parts per part of the metal squarylium complex.

9. A metal complex of a squarylium compound represented by formula (Ia)

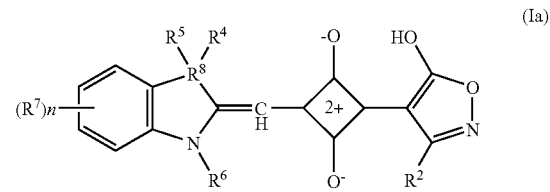

(wherein $R^2$ represents an optionally substituted alkyl, an optionally substituted aralkyl, an optionally substituted aryl, or an optionally substituted heterocyclic group;

$R^4$ and $R^5$ independently represent a hydrogen atom or an optionally substituted alkyl, an optionally substituted aralkyl, or an optionally substituted aryl group; or when $R^8$ is a carbon atom, $R^4$ and $R^5$ may form an alicyclic hydrocarbon ring or a heterocyclic ring together with the adjacent carbon atom;

$R^6$ represents a hydrogen atom or an optionally substituted alkyl, an optionally substituted aralkyl, or an optionally substituted aryl group;

all $R^7$ are independently selected from the group consisting of a halogen atom, an optionally substituted alkyl, an optionally substituted aralkyl, or an optionally substituted aryl group, a nitro group, a cyano group, and an optionally substituted alkoxy group; n denotes an integer of from 0 to 4; and when n is an integer of from 2 to 4, two adjacent $R^7$'s and the respective two adjacent carbon atoms may together form an optionally substituted aromatic ring; and $R^8$ denotes a carbon atom, a sulfur atom, a nitrogen atom, or an oxygen atom, with the proviso that when $R^8$ is a sulfur atom or an oxygen atom, $R^4$ and $R^5$ do not exist; and that when $R^8$ is a nitrogen atom, $R^5$ does not exist), and wherein the metal in the metal complex is aluminum or beryllium.

10. The metal complex of a squarylium compound according to claim 9, wherein the metal is aluminum.

11. A metal complex of a squarylium compound represented by formula (Ib)

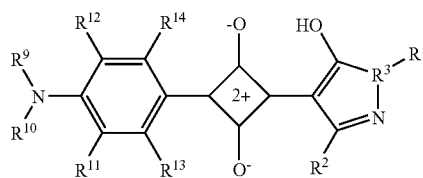

(1b)

(wherein $R^1$ and $R^2$ independently represent an optionally substituted alkyl, an optionally substituted aralkyl, an optionally substituted aryl, or an optionally substituted heterocyclic group;

$R^3$ represents a nitrogen atom or an oxygen atom, with the proviso that when $R^3$ is an oxygen atom, $R^1$ does not exist;

$R^9$ and $R^{10}$ independently represent a hydrogen atom or an optionally substituted alkyl group; or $R^9$ and $R^{10}$ may form a heterocyclic ring together with the adjacent nitrogen atom; and $R^{11}$, $R^{12}$, $R^{13}$, and $R^{14}$ independently represent a hydrogen atom, an optionally substituted alkyl or an optionally substituted alkoxy group, a hydroxyl group, or a halogen atom; and $R^9$ and $R^{12}$, or $R^{10}$ and $R^{11}$ may form an optionally substituted heterocyclic ring together with the adjacent N—C—C), and wherein the metal in the metal complex is aluminum or beryllium.

12. The metal complex of a squarylium compound according to claim 11, wherein the metal is aluminum.

13. A metal complex of a squarylium compound represented by formula (Ic)

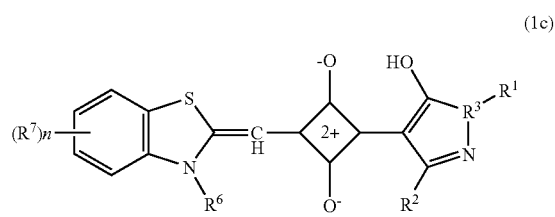

(1c)

(wherein $R^1$ and $R^2$ independently represent an optionally substituted alkyl, an optionally substituted aralkyl, an optionally substituted aryl, or an optionally substituted heterocyclic group;

$R^3$ represents a nitrogen atom or an oxygen atom, with the proviso that when $R^3$ is an oxygen atom, $R^1$ does not exist;

$R^6$ represents a hydrogen atom or an optionally substituted alkyl, an optionally substituted aralkyl, or an optionally substituted aryl group; and all $R^7$ are independently selected from the group consisting of a halogen atom, an optionally substituted alkyl, an optionally substituted aralkyl, or an optionally substituted aryl group, a nitro group, a cyano group, and an optionally substituted alkoxy group; n denotes an integer of from 0 to 4; and when n is an integer of from 2 to 4, two adjacent $R^7$'s and the respective two adjacent carbon atoms may together form an optionally substituted aromatic ring), and wherein the metal in the metal complex is aluminum or beryllium.

14. The metal complex of a squarylium compound according to claim 13, wherein the metal is aluminum.

* * * * *

UNITED STATES PATENT AND TRADEMARK OFFICE
CERTIFICATE OF CORRECTION

| | |
|---|---|
| PATENT NO. | : 7,368,224 B2 |
| APPLICATION NO. | : 10/508528 |
| DATED | : May 6, 2008 |
| INVENTOR(S) | : Tsuguo Yamaoka et al. |

It is certified that error appears in the above-identified patent and that said Letters Patent is hereby corrected as shown below:

ON THE TITLE PAGE [56] REFERENCES CITED:

Foreign Patent Documents,
"EP 1449890 8/2004" should read --EP 1 449 890 8/2004-- and
"EP 1113335 A1 * 7/2001" should read --EP 1 113 335 A1 * 7/2001--.

COLUMN 2:

Line 6, "exist)" should read --exist).--.

COLUMN 3:

Line 2, "[1] to [4]," should read --[1] to [4], wherein--.

COLUMN 4:

Line 26, "bycyclic" should read --bicyclic--; and
Line 61, "bycyclic" should read --bicyclic--.

COLUMN 6:

Line 14, "includes" should read --include--.

UNITED STATES PATENT AND TRADEMARK OFFICE
CERTIFICATE OF CORRECTION

PATENT NO. : 7,368,224 B2  
APPLICATION NO. : 10/508528  
DATED : May 6, 2008  
INVENTOR(S) : Tsuguo Yamaoka et al.

Page 2 of 3

It is certified that error appears in the above-identified patent and that said Letters Patent is hereby corrected as shown below:

COLUMN 7:

Tables 3-1,

" 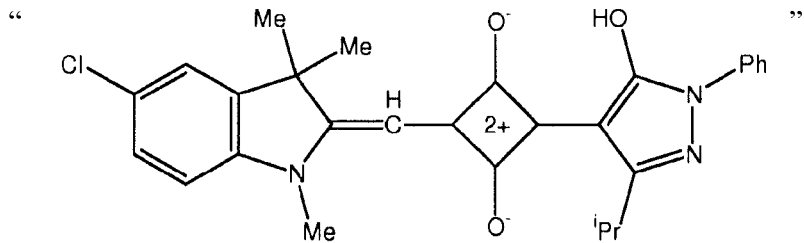 "

should read

-- 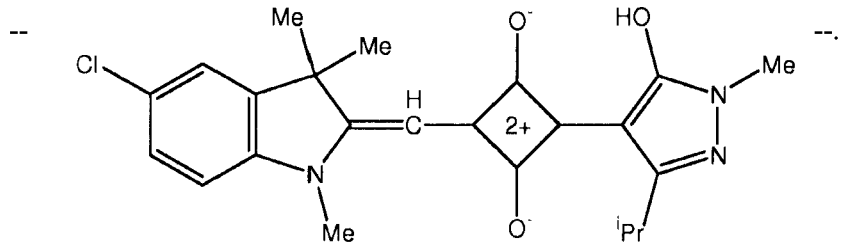 --.

COLUMN 14:

Line 15, "aid" should read --acid--; and  
Line 17, "aid" should read --acid--.

UNITED STATES PATENT AND TRADEMARK OFFICE
CERTIFICATE OF CORRECTION

PATENT NO. : 7,368,224 B2
APPLICATION NO. : 10/508528
DATED : May 6, 2008
INVENTOR(S) : Tsuguo Yamaoka et al.

It is certified that error appears in the above-identified patent and that said Letters Patent is hereby corrected as shown below:

COLUMN 15:

Line 25, "filtering the" should read --filtering. The--.

COLUMN 17:

Line 64, "triacryrate," should read --triacrylate,--.

Signed and Sealed this

Eighteenth Day of November, 2008

JON W. DUDAS
*Director of the United States Patent and Trademark Office*